United States Patent
Petersheim (10) Patent No.: US 10,098,677 B2
(45) Date of Patent: Oct. 16, 2018

(54) SPINAL PLATE

(75) Inventor: Samuel Petersheim, Elverson, PA (US)

(73) Assignee: Globus Medical, Inc., Audubon, PA (US)

( * ) Notice: Subject to any disclaimer, the term of this patent is extended or adjusted under 35 U.S.C. 154(b) by 273 days.

(21) Appl. No.: 13/226,092

(22) Filed: Sep. 6, 2011

(65) Prior Publication Data
US 2013/0060291 A1    Mar. 7, 2013

(51) Int. Cl.
| A61B 17/84 | (2006.01) |
| A61B 17/80 | (2006.01) |
| A61B 17/70 | (2006.01) |
| A61B 17/86 | (2006.01) |
| A61B 17/88 | (2006.01) |
| A61B 17/064 | (2006.01) |

(52) U.S. Cl.
CPC ...... *A61B 17/8033* (2013.01); *A61B 17/7059* (2013.01); *A61B 17/8042* (2013.01); *A61B 17/8052* (2013.01); *A61B 17/846* (2013.01); *A61B 17/8605* (2013.01); *A61B 17/8872* (2013.01); *A61B 17/0642* (2013.01)

(58) Field of Classification Search
CPC . A61B 17/80; A61B 17/8061; A61B 17/8033; A61B 17/8042; A61B 17/8047
USPC ...................... 606/70–71, 280–299
See application file for complete search history.

(56) References Cited

U.S. PATENT DOCUMENTS

| 2,133,859 | A | | 10/1938 | Hawley | |
| 3,352,190 | A | * | 11/1967 | Carlson | ......................... 411/403 |
| 5,275,601 | A | * | 1/1994 | Gogolewski | ....... A61B 17/8052 |
| | | | | | 411/399 |
| 6,193,721 | B1 | * | 2/2001 | Michelson | ...................... 606/70 |
| 6,228,085 | B1 | | 5/2001 | Theken et al. | |
| 6,746,450 | B1 | | 6/2004 | Wall et al. | |
| 9,161,795 | B2 | * | 10/2015 | Clasbrummel | ...... A61B 17/863 |
| 2003/0083660 | A1 | * | 5/2003 | Orbay | .................... A61B 17/68 |
| | | | | | 606/281 |
| 2004/0116930 | A1 | | 6/2004 | O'Driscoll et al. | |
| 2004/0127901 | A1 | | 7/2004 | Huebner et al. | |
| 2005/0187551 | A1 | * | 8/2005 | Orbay | ................ A61B 17/8033 |
| | | | | | 606/281 |

(Continued)

FOREIGN PATENT DOCUMENTS

| EP | 0599640 A1 | 6/1994 |
| JP | 6-277228 | 10/1994 |

(Continued)

*Primary Examiner* — Zade Coley
*Assistant Examiner* — Jessica Weiss (57) ABSTRACT

Spinal plates with additional features to improve the stability of the interface between the plate and the underlying bone. A bone plate may include one or more sharp ridges along the periphery of its underside. When attached to bone, the ridge digs into the bone and increases stability. A bone plate may alternatively or additionally include one or more holes for optional spikes, which may be inserted once the plate is attached to the bone. By separating the spikes and including them as an optional component, the plate may enhance stability while reducing or eliminating the chance of the spike injuring the patient. Furthermore, bone screws may incorporate alternating notches and ridges into the head of the screw. The notches and ridges may interface with a set screw, thereby preventing rotation and loosening of the screw.

11 Claims, 5 Drawing Sheets

(56) References Cited

U.S. PATENT DOCUMENTS

| | | | |
|---|---|---|---|
| 2005/0261690 A1* | 11/2005 | Binder et al. ............... 606/69 |
| 2006/0106387 A1* | 5/2006 | Fanger ............... A61B 17/7059 |
| | | | 606/281 |
| 2007/0123885 A1* | 5/2007 | Kirschman ........ A61B 17/7059 |
| | | | 606/279 |
| 2009/0012570 A1 | 1/2009 | Zhang et al. |
| 2010/0121382 A1 | 5/2010 | Weiman |
| 2010/0292737 A1* | 11/2010 | Suh ................... A61B 17/8033 |
| | | | 606/286 |
| 2011/0022097 A1* | 1/2011 | Walker et al. ............... 606/296 |
| 2011/0087229 A1 | 4/2011 | Kubiak et al. |
| 2013/0165981 A1* | 6/2013 | Clasbrummel .... A61B 17/8033 |
| | | | 606/289 |

FOREIGN PATENT DOCUMENTS

| | | | |
|---|---|---|---|
| JP | 2004-500156 | 1/2004 |
| JP | 2008-520272 | 6/2008 |
| WO | 200103570 A2 | 1/2001 |
| WO | 2010008593 A1 | 1/2010 |
| WO | WO 2011/076205 * | 6/2011 | ............. A61B 17/80 |

* cited by examiner

SPINAL PLATE

BACKGROUND OF THE DISCLOSURE

1. Field of the Disclosure

The disclosure relates to devices for immobilizing two or more vertebrae relative to one another to promote fusion of the vertebrae. The devices and improvements described herein may also be used with other types of bone plates or instrumentation.

2. Related Art

Adjacent vertebrae may be surgically joined together in a fusion procedure. The procedure may join two (bi-level) or more (multi-level) vertebrae. During the surgery, the vertebrae are fixed in position relative to one another with a plate or other instrumentation, and a bone graft is placed between the vertebrae. The bone graft will promote new bone growth between the vertebrae, and eventually the bones will grow together, which typically takes 6-18 months after the surgery.

More commonly, fusion of vertebrae is used as part of a treatment for a herniated disc, rheumatoid arthritis, infection, tumor, or other condition resulting in spinal deformities. In each case, the primary disease is treated before the fusion procedure. In the case of a herniated disc or degenerative disc disorder, for example, the intervertebral disc is removed (a procedure known as a discectomy). After the discectomy, the instrumentation is attached to the vertebrae. The two related procedures are typically performed as part of the same surgery, to minimize trauma and expense to the patient.

Many devices are available for instrumentation of the spine in a fusion procedure. Current spinal plates, however, suffer from one or more limitations. For example, there are often situations and size restrictions that limit the number of screws that can be used in a design or surgery. Fewer screws results in lower stability of the plate.

One solution to this problem has been to add spikes or other sharp features to the plate. The spikes increase the stability of the bone-plate interface, as well as the stability of the underlying bone structures. There is a risk, however, that the sharp features may puncture or damage blood vessels, nerves, or other delicate anatomical structures during placement. There is also a difficulty for the surgeon to determine how well the plate will rest on the bone surface without first inserting the spikes into the bone.

Spinal plates are commonly fixed to bone with bone screws. Many modern plate designs incorporate blocking set screws, which prevent the bone screws from backing out of the bone after they have been implanted. Blocking set screws, however, do not prevent the bone screws from rotating. It is possible for the bone screws to rotate and loosen while they are held in place by the set screws. Loose bone screws reduce the stability of the bone-plate interface, thereby reducing the chance of a successful fusion procedure.

Accordingly, there is a need for a bone plate that provides enhanced stability and prevents rotation of the bone screws holding the plate to the bone.

SUMMARY OF THE DISCLOSURE

The disclosure meets the foregoing need and allows increased safety and/or stability using advanced bone plates, which results in a significant increase in positive patient outcomes and other advantages apparent from the discussion herein.

Accordingly, in one aspect of the disclosure, a bone plate includes a bottom that contacts the bone, a top that faces away from the bone, and one or more sides that connect the top and bottom. The bone plate also includes a hole for a bone screw to attach the plate to a bone, and a ridge connected to the bottom of the plate. The ridge may be inserted into the bone.

The bone plate may also include a set screw to retain the bone screw in the bone plate. The ridge may be flush with the side, inset from the side, or located on a ring around the periphery of the bottom. The bone plate may include multiple ridges. The bone plate may include a first ridge that may be inset from the side and a second ridge that may be flush with the side.

According to another aspect of the disclosure, a bone plate includes a body, a first hole in the body, and a second hole in the body. The first hole may be configured to receive a spike, and the second hole may be configured to receive a bone screw.

The bone plate may include a set screw for retaining the bone screw in the plate. The bone plate may also include a ridge in the first hole for retaining the spike in the bone plate.

In yet another aspect of the disclosure, a bone screw, for use with a bone plate having a set screw, may include a head with an outer surface. Ridges and notches alternate on the outer surface of the head. The ridges and notches may be contacted by the set screw to prevent rotation of the bone screw.

The bone screw may include one or more bone threads. The head of the bone screw may include a socket that is configured to receive a tool. The bone screw may be used with a bone plate. The bone screw may be provided as a part of a kit that also includes a bone plate and a set screw. The kit may include multiple set screws and multiple bone screws. Furthermore, the number of the set screws may be equal to the number of bone screws.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DISCLOSURE

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

The terms "including", "comprising" and variations thereof, as used in this disclosure, mean "including, but not limited to", unless expressly specified otherwise.

The terms "a", "an", and "the", as used in this disclosure, mean "one or more", unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

An incision, which may be no more than, e.g., about two inches long, may be made in a patient to perform a fusion of adjacent vertebrae. All instrumentation should pass through this incision, which naturally limits the size of bone plates and other hardware that may be used in the procedure. In certain situations, this size restriction can result in the use of a plate with a suboptimal amount of bone screws. Screws may be omitted due to difficulties in inserting the screws and other hardware through the incision. In other situations, the plate itself may only accept a suboptimal number of screws. Adding an optimal number of holes may make the plate too big to fit through the incision or otherwise satisfy space restrictions. Other situations and circumstances may also limit the number of screws used to attach a bone plate.

FIGS. 1A-4C and 7 show various examples of a bone plate 100 (100A, 100B, 100C, 100D, 100E) that may be implemented in spine fusion procedures to provided added stability in, e.g., the afore-noted situations. The bone plate 100 includes side walls 107 (107A, 107B), a top surface 108 (108A, 108B, 108C, 108D), and a bottom surface 109 (109A, 109B, 109C, 109D). The bone plate 100 may include one or more holes 101 that are configured to receive respective one or more bone screws (such as, e.g., the bone screw 300, shown in FIGS. 7-9B). The bone plate 100 may further include a central hole 104. The bone plate 100 may also include one or more receivers 110 that are configured to receive respective one or more set screws 102. The set screws 102 may help to retain the bone screws in the bone plate 100 and the bone (not shown), preventing the screws from loosening.

Figure 1A:
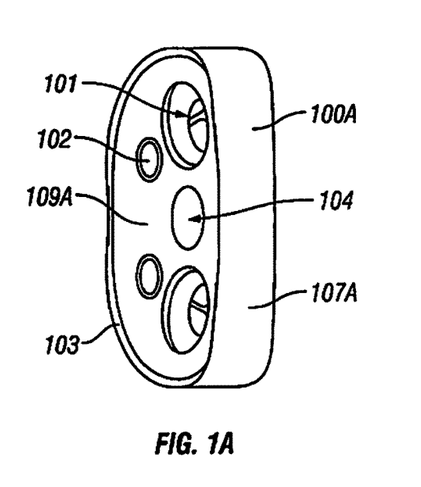
FIG. 1A shows a perspective view of an underside of a bone plate with a ridge that is flush with the sides of the bone plate.
Figure 1B:
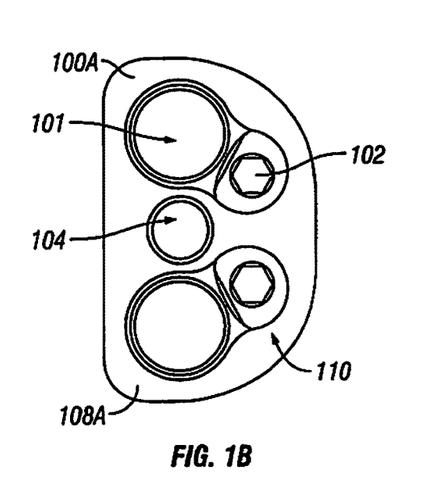
FIG. 1B shows a top-view of the bone plate of FIG. 1A.

Referring to FIGS. 1A-1B, the bone plate 100A may include a ridge 103A for added stability. The wall(s) of the ridge 103A may be tapered. The ridge 103A may be formed along (or near) a perimeter of the bone plate 100A. The ridge 103A may run along the entire perimeter of the bone plate 100A, or only a portion of the perimeter of the bone plate 100A. The bone plate 100A may be integrally formed with the ridge 103A. In particular, the bottom surface 109A of the bone plate 100A may be integrally formed with the ridge 103A.

FIG. 1A shows a perspective view of the underside, or bottom surface 109A, of the bone plate 100A, which is constructed with the ridge 103A being substantially flush with the side walls 107A of the bone plate 100A. The walls of the ridge 103A are tapered to form a substantially sharp edge along the perimeter of the ridge 103A.

FIG. 1B shows a view of the top surface 108A of the bone plate 100A. The ridge 103A is not visible in this top view, since the outer walls of the ridge 103A are substantially flush with the side walls 107A of the bone plate 100A.

Figure 2A:
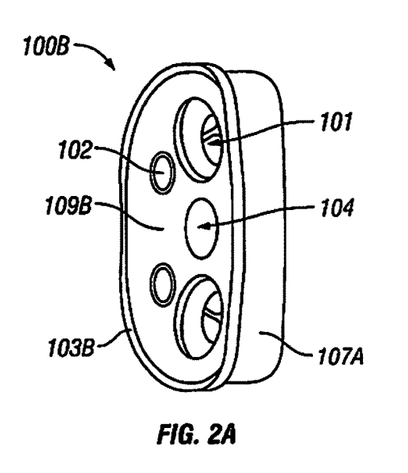
FIG. 2A shows a perspective view of a bone plate with a ridge that is located on a ring that extends past the outside edge of the bone plate.
Figure 2B:
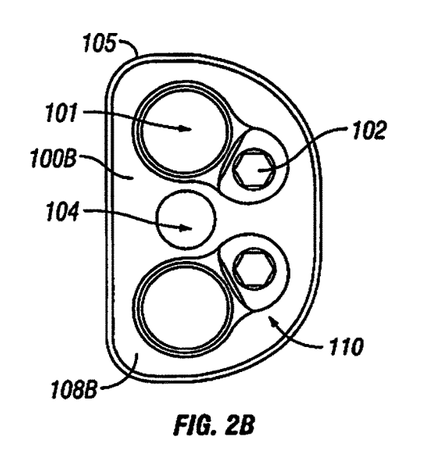
FIG. 2B shows a top-view of the bone-plate of FIG. 2A.

FIGS. 2A-2B show a bone plate 100B with a ring 105 and a ridge 103B, both of which may be integrally formed with the bone plate 100B. The ridge 103B may be formed on the ring 105, along the perimeter of the ring 105. The ring 105 may extend beyond the walls 107A of the bone plate 100B. The ring 105 may also extend beyond the bottom surface 109B of the bone plate 100B.

FIG. 2A shows a perspective view of the bottom surface 109B of the bone plate 100B, including the ridge 103B and the ring 105. As seen, the ridge 103B may include an inner wall that is configured to taper from the bottom surface 109B of the bone plate 100B (or the bottom surface of the ring 105) to the edge (or end) of the ridge 103B. Further, the ridge 103B may include an outer wall(s), which may be formed on the bottom surface of the ring 105, or which may be formed as part of the outer wall of the ring 105. The ring 105 may include an outer wall that may be substantially normal to the bottom surface 109B and substantially parallel to the walls 107A of the bone plate 100B. The outer wall of the ring 105 may be angled so as to taper off to an edge (or end) with the inner wall of the ridge 103B.

FIG. 2B shows a view of the top surface 108B of the bone plate 100B, including the ring 105. As seen, the ring 105 may be visible from the top view of the bone plate 100B.

Figure 3A:
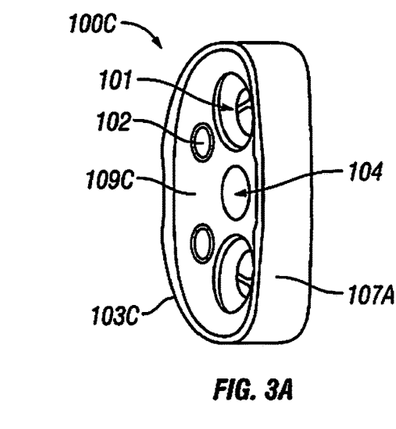
FIG. 3A shows a perspective view of a bone plate with a ridge that is inset from the outer edge of the plate.
Figure 3B:
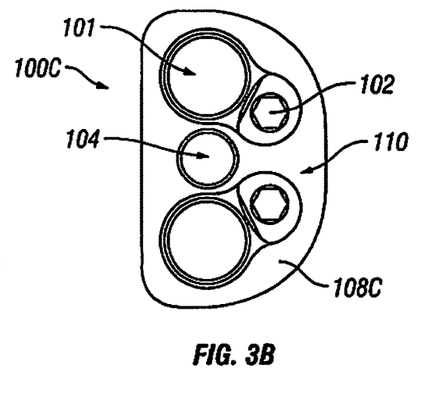
FIG. 3B shows a top-view of the bone plate of FIG. 3A.

FIGS. 3A-3B show a bone plate 100C with a ridge 103C that is formed inward of the perimeter of the bottom surface 109C. In particular, the ridge 103C is formed in the bone plate 100C so as to be inset from walls 107A of the bone plate 100C. One or both of the inner and outer walls of the ridge 103C may be tapered, so that wall(s) of ridge 103C taper off along a normal (or perpendicular) path from the bottom surface 109C to the edge (or end) of the ridge 103C.

FIG. 3A shows a perspective view of the bottom surface 109C, including the ridge 103C. As seen, the ridge 103C is inset from the walls 107A of the bone plate 100C.

FIG. 3B shows a view of the top surface 108C of the bone plate 100C. In this view, the ridge 103C is not visible.

While each of the figures shows only one ridge 103 (103A, 103B, 103C), those skilled in the art will recognize that multiple ridges 103 may be used without departing from the spirit or scope of the specification, including the attached claims. In particular, two or more ridges 103 may be used. For example, the ridge 103A of FIG. 1A may be combined with the ridge 103B of FIG. 2A to produce a bone plate 100 that includes a pair of ridges 103A, 103B (not shown). In addition, multiple ridges 103B may be located on the ring 105 shown in FIGS. 2A and 2B. The above is not an exhaustive list of the possible or contemplated examples, and further aspects will be apparent to those skilled in the art.

The inner wall and/or the outer wall of the ridge 103 (103A, 103B, 103C) may be tapered to a sharp edge (or end). The ridge 103 may also have a substantially sharp edge that is formed by substantially parallel inner and outer walls of the ridge 103 (not shown). Thus, by firmly attaching a bone plate 100 with a ridge 103 to, e.g., an underlying bone, using, e.g., a bone screw, the ridge 103 may contact and penetrate (or dig into) the bone. With the ridge 103 successfully implanted into the bone, lateral sliding of the bone plate 100 on the bone may be substantially or completed reduced or eliminated. The use of multiple ridges 103 may further enhance the anti-sliding effect of the ridges 103.

In addition, the ridge 103 may strengthen the bone-plate interface in additional ways. When the bone plate 100 is applied over multiple vertebrae, for example, the ridge 103 may work with the bone screws to prevent the vertebrae from moving relative to one another. Furthermore, the ridge 103 may be treated with a coating, such as, e.g., hydroxyapatite coating, titanium plasma spray, to encourage bony on-growth, which may stabilize or strengthen the interface between the plate and the underlying bone.

The improved stability imparted by a ridge 103 may have one or more effects on the use or design of the bone plate 100. As stated previously, the need for screws may be reduced. As a result, fewer screws may be used to secure the bone plate 100 to a bone, without compromising stability. Similarly, the size of the bone plate 100 may be reduced without a reduction in stability. A smaller bone plate 100 will likely require a smaller incision, which in turn may cause less trauma to the patient and improve recovery time.

Figure 4A:
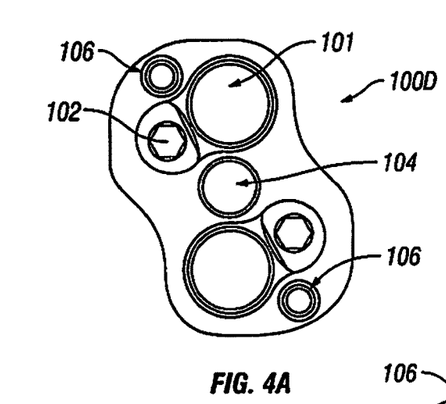
FIGS. 4A, 4B, and 4C show various views of a bone plate that is constructed to receive optional bone spikes.
Figure 4B:
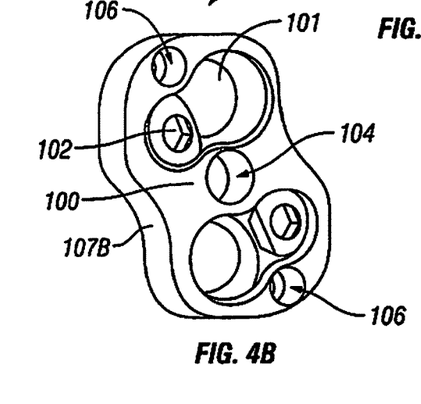
Figure 4C:
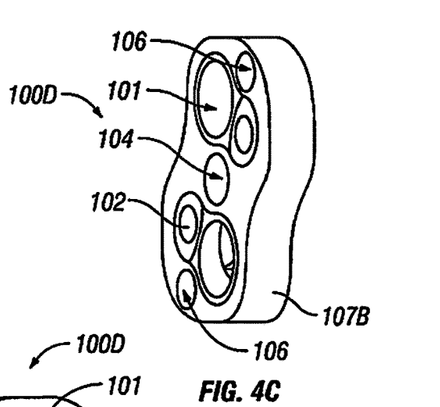

According to a further aspect of the disclosure, the bone plate 100 may include one or more sharp spikes to improve stability. The function of the spike is similar to that of the ridge 103 described above, but the spike may extend further away from the bone plate 100. FIGS. 4A, 4B, and 4C show various views of the bone plate 100D. The bone plate 100D is configured to receive one or more spikes. In particular, the bone plate 100D is configured to receive one or more optional spikes 206 that may be inserted in and through one or more respective openings 106 (in the bone plate 100D) and into, e.g., the bone (not shown). Once the bone plate 100D is securely attached to the bone with bone screws (e.g., the bone screws 300, shown in FIG. 7), one or more optional spikes 206 may be inserted through the spike holes 106 with a special tool 200 (shown in FIGS. 5A-6B).

Referring to FIGS. 5A-6B, the tool 200 includes a body 201, a plunger 202, and a shaft 203. The shaft 203 may run through the center and along the length of the body 201 and connect to the plunger 202 at a proximal end of the tool 200. The tool 200 is configured so that when the plunger 202 is depressed by, e.g., a surgeon, the shaft 203 is caused to move and extend from the distal end of the tool 200. Likewise, when the plunger 202 is in an extended position, the shaft 203 may be retracted from the distal end of the tool 200 by, e.g., a pulling force.

At the distal end of the tool 200, the shaft 203 may pass through a ring 204, which may act as a base for two or more panels 205. The distal end of the tool 200 may also be provided with slits. The interior of the panels 205 and the distal end of the shaft 203 may be designed in such a way that they close together, forming a continuous shape, when the plunger 202 is in a retracted position (i.e. when the plunger 202 is extended, shown in FIG. 5A). In addition, depressing the plunger 202 and extending the shaft 203 may cause the panels 205 to separate, as shown in FIG. 6B. For example, the distal end of the shaft 203 may have a tapered shape that presses against the interior walls of the panels 205 as the shaft 203 is extended.

The panels 205, the distal end of the shaft 203, or both may be configured to retain an optional spike 206 for use with the bone plate 100D shown in FIGS. 4A-4C. For example, the shaft 203 may be magnetized. In this instance, the shaft 203 may be used to pick up and easily retain a spike 206 that is manufactured from a ferromagnetic material. The panels 205 may contain an interior notch or ridge for gripping the spike 206 when the panels 205 are in a closed position. In addition, the panels 205 may be biased by a spring or other mechanism (not shown), enabling the panels 205 to grip the spike 206 with considerable force.

Figure 5A:
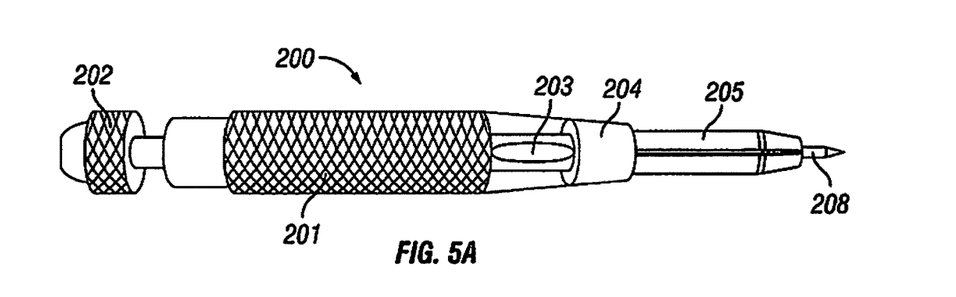
FIG. 5A shows a tool for inserting a spike into the plate shown in FIG. 4A with the plunger in an extended position.
Figure 5B:
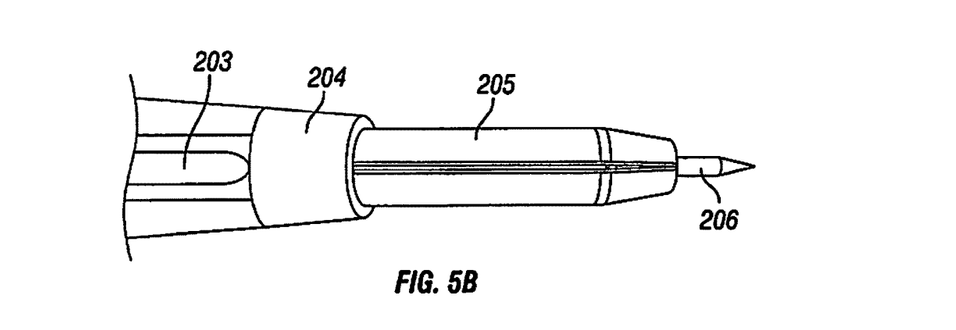
FIG. 5B shows a close-up view of the distal end of the tool of FIG. 5A.

FIG. 5A shows the spike tool 200 with the plunger 202 in an extended position. The distal end of the shaft 203 is retracted and the panels 205 are closed. The panels 205 are holding a spike 206 for use with the bone plate 100D shown in FIGS. 4A-4C. FIG. 5B provides a magnified view of the distal end of the tool 200, which shows an example of how the panels 205 may come together.

A tool 200 in this configuration may be used to insert a spike 206 through a spike hole 106 of the bone plate 100D. The hole 106 may be configured to mechanically engage and retain the spike 206 after it has passed a certain point. For example, the hole 106 may include a beveled ridge or ridges that allows the spike 206 to pass the ridge as it is inserted, yet prevents the spike 206 from working free of the hole 106. Additionally or alternatively, the hole 106 may include a ridge or notch that serves as a lower limit for the spike 206. In this instance, the spike may be prevented from being inserted through this ridge or notch. The limit ridge and the beveled ridge may work together to substantially fix the spike 206 in place, maximizing the spike's 206 contribution to the stability of the bone-plate interface and the overall construct.

Figure 6A:
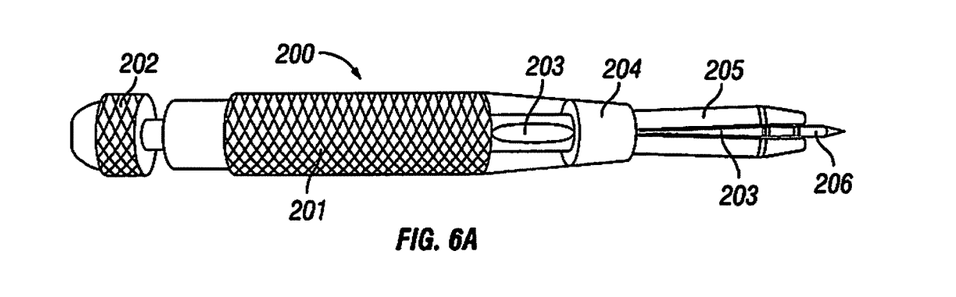
FIG. 6A shows a tool for inserting a spike into the plate shown in FIG. 4A with the plunger in a depressed position.
Figure 6B:
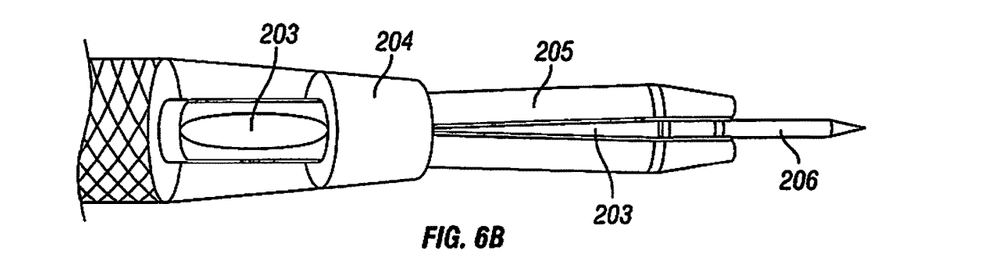
FIG. 6B shows a close-up view of the distal end of the tool of FIG. 6A.

FIG. 6A shows the tool 200 with the plunger 202 depressed and the shaft 203 extended. FIG. 6B shows a close-up of the distal end of the tool 200. Shaft 203 may force apart or separate the panels 205 while the tool 200 still retains the spike 206.

A bone plate 100D with optional spikes eliminates sharp protrusions from the plate that may injure blood vessels, nerves, and other anatomical features. In addition, the bone plate 100D may be used without some or all of the optional spikes 206 being inserted. This may allow surgeons or hospitals to reduce the number and type of bone plates 100 they keep in stock, thereby reducing costs.

Figure 7:
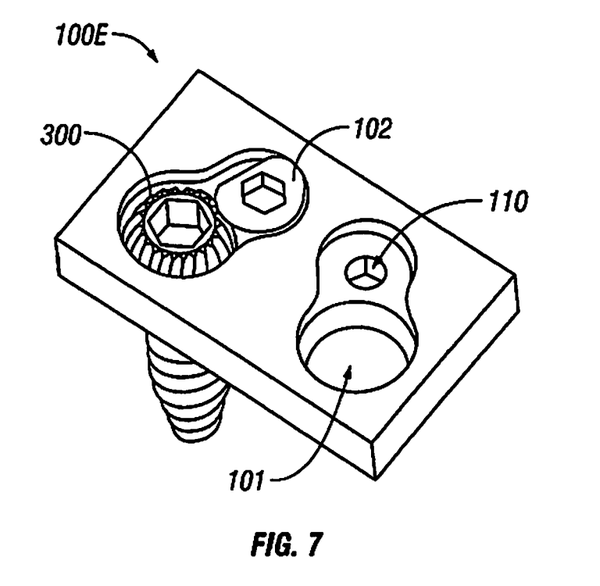
FIG. 7 shows a bone screw with a notched head.

FIG. 7 shows an example of a bone screw 300 that is constructed according to the principles of the disclosure. The bone screw 300 may include a notched head. The bone screw 300 may be used with a bone plate 100E. The bone plate 100E may be configured as any one of the bone plates 100A-100D previously described. The bone screw 300 may be used with a set screw 102 to prevent the bone screw 300 from working out of the underlying bone (not shown). As seen in FIG. 7, the bone plate 100E may include a hole 101 for receiving the bone screw 300 and a receiver 110 (such as, e.g., a hole) for receiving the set screw 102.

Figure 8:
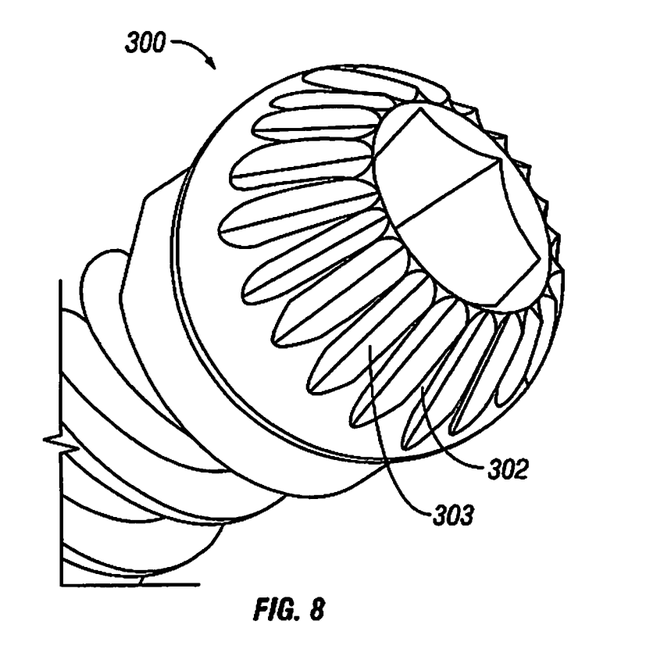
FIG. 8 shows a close-up view of the bone screw of FIG. 7.

FIG. 8 provides a close-up view of the head portion of the bone screw 300. The head portion of the bone screw 300 may include alternating ridges 302 and notches 303. This arrangement allows the set screw 102 to physically engage the head of the bone screw 300, thereby preventing both rotation and backing out of the bone screw 300 from the bone or the bone plate 100E. The bone screw 300 may also include bone threads 304, which are configured to penetrate and engage, e.g., bone.

Figure 9A:
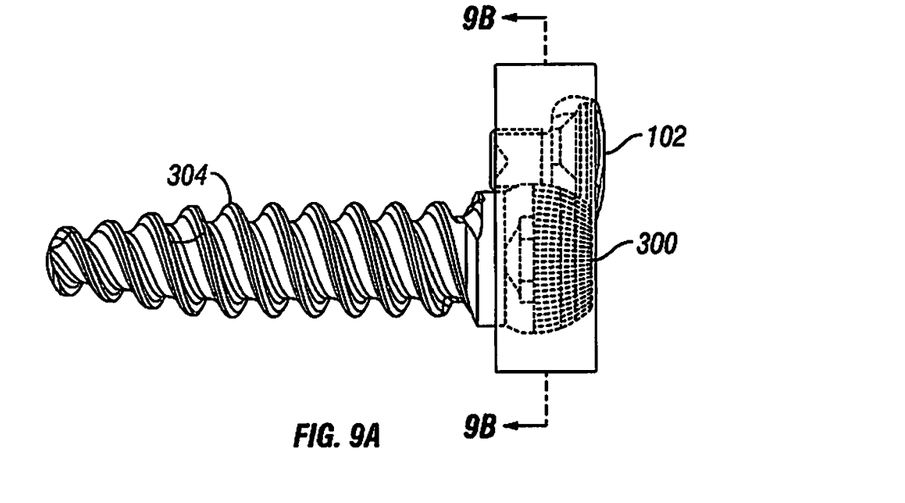
FIG. 9A shows a side view of a bone plate with a set screw and a notched-head bone screw.
Figure 9B:
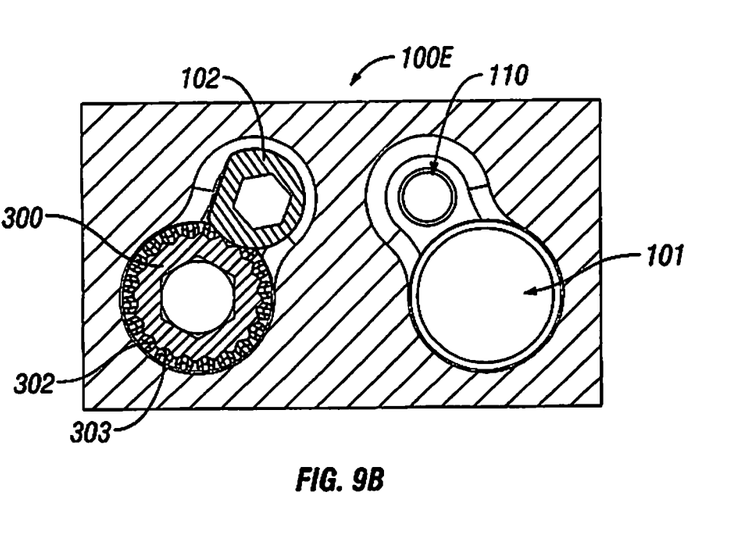
FIG. 9B is a cutaway view taken along line B-B in FIG. 9A.

FIG. 9A shows a side view of the plate 100E with a set screw 102 and bone screw 300. FIG. 9B is a cutaway view taken along line B-B. FIG. 9B shows how the set screw 102 may interface with the ridges 302 and notches 303 of the head portion of the bone screw 300. This interaction may substantially or completely prevent rotation of the bone screw 300 when the construct, including bone plate 100E, is subjected to normal biomechanical forces within the body.

It will be apparent to one skilled in the relevant arts that any of the above-described modifications may be combined. For example, a bone plate may include a sharp, peripheral ridge to enhance stability of the construct; optional spikes for further enhancing stability; and notched-head bone screws to prevent rotation of the screws inside the body. Other combinations are possible and contemplated. A bone plate or other construct or instrumentation may utilize any combination of the above-described enhancements without departing from the spirit and scope of the specification, including the attached claims.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. A bone plate assembly comprising:
   a bone plate;
   a set screw; and
   a bone screw having a head comprising an outer surface, wherein the head comprises an upper portion including an upper surface and a lower portion including a lower surface;
   wherein the bone screw further comprises a plurality of alternating ridges and notches on the outer surface of the head, the plurality of alternating ridges having a continuous apex extending from the upper surface to the lower surface of the head of the bone screw, and the plurality of alternating ridges and notches each having a longitudinal axis extending in a direction from the upper portion to the lower portion of the head such that each of the ridges and notches has a first end proximate the upper portion of the head and an opposing end proximate the lower portion of the head,
   wherein the set screw is configured to allow the bone screw to be received into the bone plate when rotated to a first position and the set screw directly engages with the ridges and notches such that at least a portion of the set screw is residing in at least one notch thereby preventing rotation of the bone screw when the set screw is rotated to a second position, and wherein a portion of a head of the set screw is positioned above the head of the bone screw when in the second position,
   wherein the head with alternating ridges and notches is at least partially spherical, and
   wherein the set screw is not configured to engage bone, and
   wherein the bone plate has a bottom surface comprising a ridge disposed along a perimeter of the bottom surface.

2. The bone plate assembly of claim 1, wherein the bone screw further comprises at least one bone-engaging thread.

3. The bone plate assembly of claim 1, wherein the head of the bone screw further comprises a socket for receiving a tool.

4. The bone plate assembly of claim 1, wherein the bone plate includes a recessed portion having a surface for engaging the set screw, and a bottom of the head of the set screw rests on the recessed portion of the bone plate.

5. The bone plate assembly of claim 1, wherein an opening extends through the bone plate to retain the bone screw, and the opening is substantially smooth.

6. The bone plate assemble of claim 1, wherein the ridge is formed around the entire perimeter of the bottom surface of the bone plate.

7. The bone plate assemble of claim 1, wherein an upper surface of the head of the set screw is positioned above the upper surface of the head of the bone screw.

8. The bone plate assembly of claim 1, wherein the head of the set screw further comprises a socket for receiving a tool.

9. A kit comprising:
   the bone plate assembly of claim 1, wherein the kit comprises a plurality of bone screws and a plurality of set screws.

10. The kit of claim 9, wherein the number of bone screws is equal to the number of set screws.

11. The kit of claim 9, wherein the set screws are asymmetrical.

* * * * *